United States Patent [19]

Watkins

[11] 4,133,961

[45] Jan. 9, 1979

[54] PROCESS FOR THE PRODUCTION OF UNSATURATED CARBOXYLIC ACIDS CONTAINING ADDITIONAL FUNCTIONAL GROUPS

[75] Inventor: Windell C. Watkins, Henderson, Tex.

[73] Assignee: Eastman Kodak Company, Rochester, N.Y.

[21] Appl. No.: 825,342

[22] Filed: Aug. 17, 1977

[51] Int. Cl.$^2$ ............................................. C07C 69/52
[52] U.S. Cl. .................................. 560/190; 260/464; 260/465.4; 560/122; 560/123; 560/124; 546/341; 546/342
[58] Field of Search ............... 560/190, 122, 123, 124; 260/295 R, 465.4, 464

[56] References Cited

PUBLICATIONS

Weintraub et al., J.A.C.S., 86, pp. 4880–4885, (1964).
Wright et al., Proc. Soc. Exptl. Biol. Med., 115, 497–504, (1964).

*Primary Examiner*—Jane S. Myers
*Attorney, Agent, or Firm*—Edward R. Weber; Daniel B. Reece, III

[57] ABSTRACT

A process for the preparation of an unsaturated dicarboxylic acid containing additional functional groups wherein a substituted cyclobutane is contacted with an anhydride of acetic, propionic or butyric acid at an elevated temperature.

7 Claims, No Drawings

PROCESS FOR THE PRODUCTION OF UNSATURATED CARBOXYLIC ACIDS CONTAINING ADDITIONAL FUNCTIONAL GROUPS

This invention relates to a process for the preparation of an unsaturated dicarboxylic acid having at least one other functional group by the reaction of a substituted cyclobutane with an anhydride of acetic, propionic or butyric acid at an elevated temperature.

The study of the alkylation and acylation of enamines stimulated interest in the chemistry of enamines. It has been found that the electrophylic olefins will react with enamines to form cyclobutanes. The most reactive enamines in this cyclo addition reaction are those which have no $\beta$-hydrogens, the simplest of which are enamines derived from isobutylaldehyde. The use of cyclobutanes derived from enamines as intermediates in organic synthesis has been limited. Most of the cyclobutanes have been found to undergo acid and magnesium halide catalyzed hydrolysis. A second synthetic use of enamine-derived cyclobutanes was in the synthesis of cyclobutanones. The amine is oxidized with bromine to an $\alpha$-bromo-$\beta$-ketone ester which is then debromonated and subsequently decarboxylated to the cyclobutanone by treatment with a base. Grignard reagents have been found to react with enamine-derived cyclobutanes to yield $\alpha$-amino ketones.

Since cyclobutanes derived from isobutyraldehyde could be a commercial commodity, it was an object of this invention to find a use for these cyclobutanes in the synthesis of commercially useful compounds.

Other objects of the invention will become apparent from consideration of the specification and claims of this application.

Cyclobutanes derived from enamines by a cyclo addition reaction have been found to react with anhydrides in a novel ring opening condensation reaction. More particularly, cyclobutanes of the type

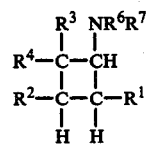

wherein
$R^1$ is lower alkoxycarbonyl, cyano or pyridyl;
$R^2$ is hydrogen or lower alkoxycarbonyl;
$R^3$ is lower alkyl;
$R^4$ is hydrogen or lower alkyl, or $R^3$ and $R^4$ in combination may be a methylene bridge containing three to five carbons; and $R^6$ and $R^7$ are lower alkyl or, in combination, tetramethylene or pentamethylene, may be reacted with an anhydride of the type

wherein $R^5$ is hydrogen, methyl or ethyl, at an elevated temperature to form an unsaturated carboxylic acid of the type

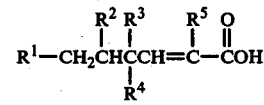

wherein $R^1$ through $R^5$ are as previously defined.

By selecting the starting enamine and olefin in the preparation of the cyclobutane and selecting the anhydride used in the ring opening condensation reaction, a variety of unsaturated carboxylic acids containing at least one other functional group may be prepared. Thus, the synthetic utility of the reaction is apparent.

In the course of the investigation of the chemistry of enamine-derived cyclobutanes, methyl 3,3-dimethyl-2-dimethylaminocyclobutanecarboxylate was found to react with acetic anhydride to give, after hydrolysis, the half ester of a dicarboxylic acid. The nmr spectrum indicated the structure of the product to be 6-carbomethoxy-4,4-dimethyl-2-hexenoic acid. The position of the double bond was uncertain. The carbon skeleton was verified by saponification of the ester and reduction of the resulting diacid to the known 4,4-dimethylpimelic acid.

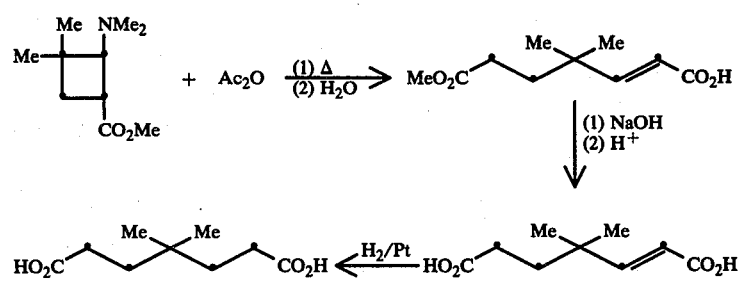

To verify the position of the double bond in the 6-carbomethoxy-4,4-dimethyl-2-hexenoic acid, diethyl 3,3-dimethyl-4-dimethylamino-1,2-cyclobutanedicarboxylate was treated with acetic anhydride. The product of this reaction was proven to be 5,6-dicarbethoxy-4,4-dimethyl-4-hexenoic acid by its nmr spectrum and not the product with the unsaturation in conjugation with the carbethoxy groups.

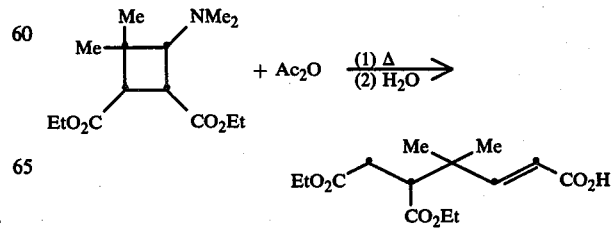

From this information, it was concluded that the postulated position of the double bond in 6-carbomethoxy-4,4-dimethyl-2-hexenoic acid is correct.

The scope of this cyclobutane ring opening was investigated to determine what types of compounds can be prepared by this method. Acetic anhydride was found to react with virtually every type of enamine-derived cyclobutane. Differing functional groups on the ring had little effect on the course of the reaction nor does the structure of the amine used in preparing the enamine.

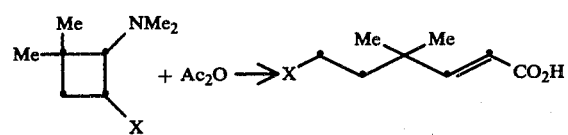

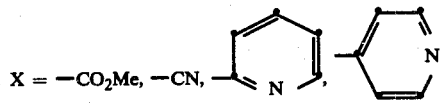

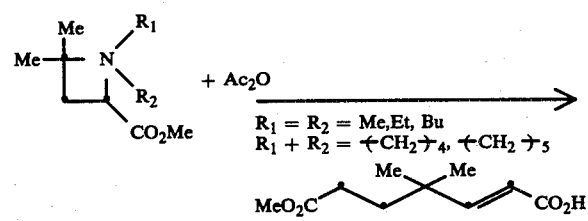

The cyclobutane could be derived from an enamine which contained a β-hydrogen as illustrated below:

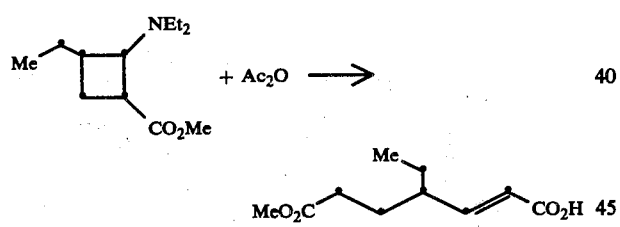

Also, fused ring cyclobutanes and spiro-cyclobutanes were found to react but could not be purified due to their extremely high boiling points. The presence of these products was verified by the nmr spectra of the mixtures isolated.

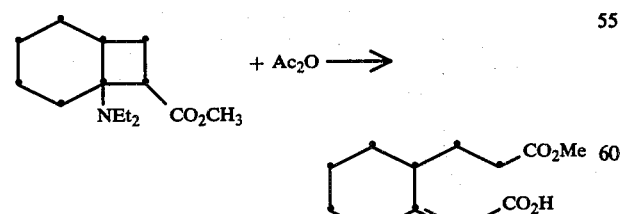

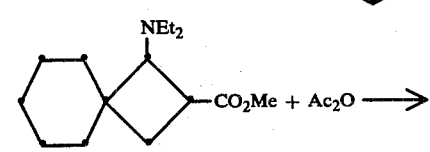

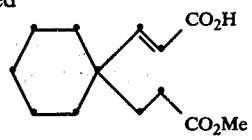

It was shown that propionic anhydride reacted with methyl 3,3-dimethyl-2-dimethylaminocyclobutanecarboxylate in a manner analogous to acetic anhydride.

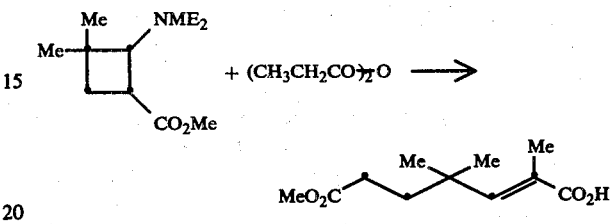

Isobutyric anhydride, dimethyl malonate and ethyl cyanoacetate were shown to react with this cyclobutane but the products could not be isolated. It is assumed that these products are analogous to the product from acetic anhydride. Nitromethane, ethyl acetoacetate and butyl acetate were found to be completely unreative with an enamine-derived cyclobutane.

In order to postulate a feasible mechanism several pieces of information about the reaction were necessary. First, the stoichiometry of the reaction was found to be that one mole of cyclobutane reacts with two moles acetic anhydride to give, before hydrolysis, one mole each of acetic acid, N,N-dimethyl acetamide and an intermediate which hydrolyzes to the observed acid. This intermediate exhibits anhydride absorption in the infrared region.

The electronic effects on the rate of reaction were studied with respect to both the amine group on the cyclobutane ring and the functional group which was present. As shown below with a series of methyl 3,3-dimethyl-2-dialkylaminocyclobutanecarboxylates, the reaction rate was found to be roughly proportional to the base strength of the amine used in preparing the starting enamine. That

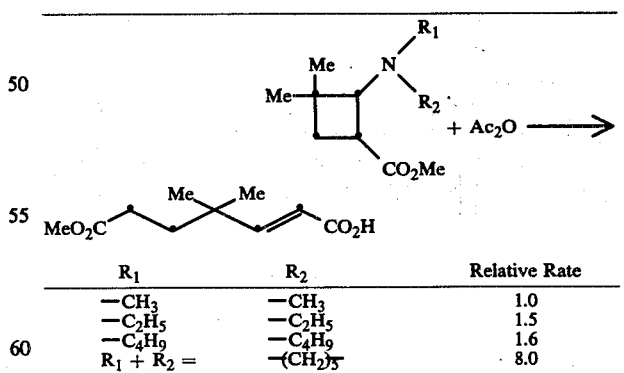

| $R_1$ | $R_2$ | Relative Rate |
|---|---|---|
| —$CH_3$ | —$CH_3$ | 1.0 |
| —$C_2H_5$ | —$C_2H_5$ | 1.5 |
| —$C_4H_9$ | —$C_4H_9$ | 1.6 |
| $R_1 + R_2 =$ | —$(CH_2)_5$— | 8.0 | is, the rate increases with increasing basicity of the cyclobutylamine. This relationship indicated the generation of a carbonium ion on the carbon attached to the nitrogen in the rate-determining step since increased basicity of the electrons on nitrogen would increase the stability of the generated ion.

The electronic effect of functional groups on the cyclobutane ring on reaction rate is shown below. It was also found that the rate of ring opening was inversely proportional to the electrophilicity of the olefin used to form the cyclobutane. The high rate exhibited by the pyridyl-substituted cyclobutane indicates a protonated species.

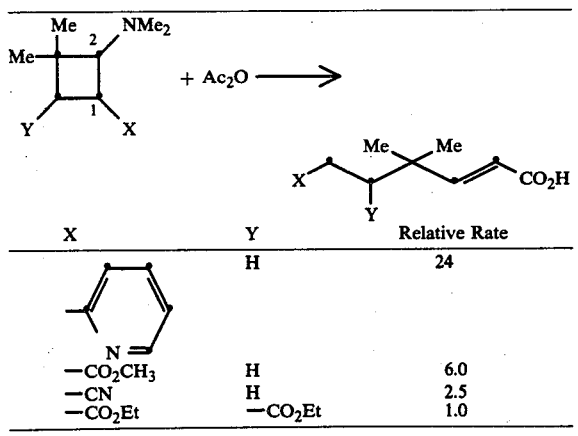

| X | Y | Relative Rate |
|---|---|---|
| pyridyl | H | 24 |
| —CO$_2$CH$_3$ | H | 6.0 |
| —CN | H | 2.5 |
| —CO$_2$Et | —CO$_2$Et | 1.0 |

These differences in rate show the increased stabilization of the bond between carbons 1 and 2 as increasingly electronegative groups are attached to the ring and this bond breakage is the rate-determining step.

The reaction proceeds well at atmospheric pressure although super- or subatmospheric pressure may be used if desired. The reaction may be conducted at a temperature of from about 30° C. to about 200° C., preferably about 120° C. to about 160° C. The ratio of cyclobutane to acid anhydride should be from about 2:1 to about 5:1, preferably about 2:1 to about 3:1. If desired, the reaction may be conducted in the presence of an inert solvent, the inert solvent being defined as any material which is a solvent for both the reactants and the products and which is inert to the reactants and the products under the conditions of the reaction. Typically aliphatic and aromatic hydrocarbons, ketones, and aliphatic and aromatic nitro compounds which have suitable boiling points are effective. Suitable solvents include toluene, xylene, mineral spirits, 4-heptanone and nitrobenzene.

The process of the invention is illustrated in greater detail by the following examples. It is understood that these examples are not intended to limit the invention in any way and obvious modification will occur to those skilled in the art.

EXAMPLE 1

Synthesis of Cyclobutanes

The procedure for the synthesis of cyclobutanes is essentially that of Brannock, et al., *J. Org. Chem.*, 26, 625 (1961). Thus, one equivalent of an enamine and 1.5 equivalent of the appropriate olefinic reactant are dissolved in acetonitrile and the mixture heated under reflux until complete disappearance of the enamine as determined by Glc analysis. The reaction mixture is concentrated on a rotary evaporator and the residue distilled under reduced pressure. Structures of the cyclobutanes are confined by their infrared and NMR spectra. The cyclobutanes listed in the following table are prepared by this procedure.

$$R^3\underset{R^4}{\diagdown}C=C\underset{H}{\diagup}\!\!\overset{R^6}{\underset{R^7}{N}}\!\!+\ R^1\underset{H}{\diagdown}C=C\underset{H}{\diagup}R^2 \longrightarrow R^2-\underset{H}{\overset{R^3}{\underset{|}{C}}}-\underset{H}{\overset{NR^6R^7}{\underset{|}{C}}}-H \\ R^4-\underset{}{C}-\underset{}{C}-R^1$$

| Cyclobutane | R$^1$ | R$^2$ | R$^3$ | R$^4$ | R$^6$ | R$^7$ | % Yield | Boiling Point, ° C. |
|---|---|---|---|---|---|---|---|---|
| I | CO$_2$Me | H | Me | Me | Me | Me | 60 | 79–82/1 mm. |
| II | CO$_2$Et | CO$_2$Et | Me | Me | Me | Me | 22 | 93–94/1.5 mm. |
| III | CO$_2$Me | H | Me | Me | ←CH$_2$→$_5$ | | 52 | 97–99/0.5 mm. |
| IV | CO$_2$Me | H | Me | Me | Bu | Bu | 64 | 75–80/0.1 mm. |
| V | CN | H | Me | Me | Me | Me | 59 | 44–45/0.5 mm. |
| VI | CN | H | Me | Me | ←CH$_2$→$_5$ | | 39 | 73–77/1 mm. |
| VII | CO$_2$Me | H | Et | H | ←CH$_2$→$_5$ | | 53 | 87–90/0.5 mm. |
| VIII | CN | H | Et | H | ←CH$_2$→$_5$ | | 66 | 101/0.2 mm. |
| IX | CO$_2$Me | H | Me | Me | Et | Et | 74 | 63–68/2 mm. |
| X | CO$_2$Me | H | Et | H | Et | Et | 74 | 75/0.8 mm. |
| XI | CO$_2$Me | H | ←CH$_2$→$_5$ | | Et | Et | 65 | 90–96/0.5 mm. |
| XII | CO$_2$Me | CO$_2$Me | Me | Me | Me | Me | 62 | 80–95/1.5 mm. |
| XIII |  | H | Me | Me | Me | Me | 68 | (mp. 51° C.) |

EXAMPLE 2

Reactions of Cyclobutanes with Anhydrides

A mixture of one equivalent of the cyclobutane and three equivalents of the anhydride are heated under reflux until complete disappearance of the cyclobutane as determined by Glc analysis. After cooling to room temperature, water is added and refluxing continued for 3 to 4 hours. The mixture is cooled, extracted with ether and the ether extract dried over magnesium sulfate. The ether is evaporated and the residue distilled under reduced pressure. The structure of the products is confirmed by their infrared and NMR spectra. The unsaturated carboxylic acids listed in the following table are prepared by this procedure.

$$\begin{matrix} R^3 & NR^6R^7 \\ R^4-\overset{|}{C}-\overset{|}{C}-H \\ R^2-\underset{|}{C}-\underset{|}{C}-R^1 \\ H & H \end{matrix} + (R^5CH_2\overset{O}{\overset{\|}{C}})_2O \xrightarrow[\text{2. } H_2O]{\text{1. heat}}$$

$$R^1-CH_2\overset{R^2}{\overset{|}{C}H}-\overset{\overset{R^3}{|}}{\underset{\underset{R^4}{|}}{C}}-CH=\overset{R^5}{\overset{|}{C}}-\overset{O}{\overset{\|}{C}}-OH$$

| Cyclobutane From Example 1 | Anhydride $R^5$ | % Yield | Melting Point, °C. | Boiling Point, °C. |
|---|---|---|---|---|
| I | H | 79 | 55–57 | 170–5/0.3 mm. |
| II | H | 35 |  | 155–160/0.3 mm. |
| VII | H | 43 |  | 140–150/1.1 mm. |
| V | H | 37 | 69–71 | 144/0.3 mm. |
| I | Me | 43 |  | 120–5/0.2 mm. |
| XI | H | 14 |  | 125–130/0.5 mm. |
| XII | H | 20 | decomp. |  |
| I | Et | 40 |  | 130–5/0.1 mm. |

The invention has been described in detail with particular reference to certain preferred embodiments thereof but it will be understood that variations and modifications can be effected within the spirit and scope of the invention.

I claim:

1. Process for the preparation of a compound having the formula $$R^1-CH_2\overset{R^2}{\overset{|}{C}H}\overset{R^3}{\underset{\underset{R^4}{|}}{\overset{|}{C}}}CH=\overset{R^5}{\overset{|}{C}}-\overset{O}{\overset{\|}{C}}OH$$

which comprises contacting a cyclobutane having the formula $$\begin{matrix} R^3 & NR^6R^7 \\ R^4-\overset{|}{C}-\overset{|}{C}-H \\ R^2-\underset{|}{C}-\underset{|}{C}-R^1 \\ H & H \end{matrix}$$

wherein
$R^1$ is lower alkoxycarbonyl, cyano or pyridyl;
$R^2$ is hydrogen or lower alkoxycarbonyl;
$R^3$ is lower alkyl;
$R^4$ is hydrogen or lower alkyl, or $R^3$ and $R^4$ in combination may be a methylene bridge containing three to five carbons; and
$R^6$ and $R^7$ are lower alkyl or, in combination, tetramethylene or pentamethylene; with an anhydride of the type $$(R^5-CH_2-\overset{O}{\overset{\|}{C}})_2-O$$

wherein $R^5$ is hydrogen, methyl or ethyl at a temperature of from about 30° C. to about 200° C. and a mole ratio of cyclobutane to acid anhydride of from about 2:1 to about 5:1.

2. The process of claim 1 wherein the ratio of cyclobutane to acid anhydride is from about 2:1 to about 3:1.

3. The process of claim 1 wherein the cyclobutane is contacted with the acid anhydride at a temperature of from about 120° C. to about 160° C.

4. The process of claim 1 wherein the cyclobutane is contacted with the acid anhydride in the presence of an inert solvent.

5. The process of claim 4 wherein the inert solvent is selected from the group consisting of aliphatic and aromatic hydrocarbons, ketones and aliphatic or aromatic nitro compounds.

6. The process of claim 4 wherein the inert solvent is selected from the group consisting of toluene, xylene, mineral spirits, 4-heptanone, and nitrobenzene.

7. The process of claim 1 wherein methyl 3,3-dimethyl-2-dimethylaminocyclobutanecarboxylate is reacted with acetic anhydride to produce 6-carbomethoxy-4,4-dimethyl-2-hexenoic acid.

* * * * *